United States Patent
Inglis et al.

(10) Patent No.: US 6,541,009 B1
(45) Date of Patent: Apr. 1, 2003

(54) VIRAL VACCINES

(75) Inventors: Stephen Charles Inglis, Linton (GB); Michael Edward Griffith Boursnell, Cambridge (GB); Anthony Charles Minson, Great Shelford (GB)

(73) Assignee: Xenova Research Limited, Cambridge (GB)

( * ) Notice: Subject to any disclaimer, the term of this patent is extended or adjusted under 35 U.S.C. 154(b) by 0 days.

(21) Appl. No.: 08/462,632

(22) Filed: Jun. 5, 1995

Related U.S. Application Data

(62) Division of application No. 08/384,963, filed on Feb. 7, 1995, now Pat. No. 5,665,362, which is a continuation of application No. 08/030,073, filed as application No. PCT/GB91/01632 on Sep. 23, 1991, now abandoned.

(30) Foreign Application Priority Data

Sep. 25, 1990 (GB) ............................................ 9020799
Mar. 8, 1991 (GB) ............................................ 9104903

(51) Int. Cl.[7] ...................... A61K 39/295; A61K 39/245
(52) U.S. Cl. ............................... 424/199.1; 424/205.1; 424/229.1
(58) Field of Search .......................... 424/199.1, 205.1, 424/229.1, 231.1; 435/172.3, 235.1; 935/240.2, 65

(56) References Cited

U.S. PATENT DOCUMENTS 4,996,152 A * 2/1991 Carter et al. .............. 435/172.3
5,338,683 A * 8/1994 Paoletti ..................... 435/320.1
5,494,807 A * 2/1996 Paoletti et al. ............. 435/69.3

FOREIGN PATENT DOCUMENTS

| EP | 0213894 | 3/1987 |
|---|---|---|
| EP | 0386882 | 9/1990 |
| EP | 0453242 | 10/1991 |
| WO | WO 8909271 | 10/1989 |
| WO | WO 9005538 | 5/1990 |
| WO | WO 9010693 | 9/1990 |
| WO | WO 9105055 | 4/1991 |
| WO | 9205263 | 4/1992 |
| WO | WO 9403207 | 2/1994 |

OTHER PUBLICATIONS

Hutchinson et al. "A Novel Herpes Simplex Virus Glycoprotein, gL, Forms a Complex with Glycoprotein H (gH) and Affects Normal Folding and Surface Expression of gH". Journal of Virology. vol. 66, No. 4, pp. 2240–2250, Apr. 1992.*

Schranz et al. "A Viable HSV–1 Mutant Deleted in Two Nonessential Major Glycoproteins". Virology. vol. 170, pp. 273–276, 1989.*

Haj–Ahmad et al. "Development of a Helper–Independent Human Adenovirus Vector and Its Use in the Transfer of the Herpes Simplex Virus Thymidine Kinase Gene". Journal of Virology. vol. 57, No. 1, pp. 267–274, Jan. 1986.*

Weber et al. "Rapid identification of Nonessential Genes of Herpes Simplex Virus Type 1 by Tn5 Mutagenesis". Science. vol. 236, pp. 576–579, May 1, 1987.*

Ligas et al. "A Herpes Simplex Virus Mutant in Which Glycoprotein D Sequences Are Replaced by Beta–Galactosidase Sequences Binds to but Is Unable To Penetrate into Cells". Journal of Virology. vol. 62, No. 5, pp. 1486–1494, May 1988.*

U.S. pat. 5,166,057. Palese et al. Recombinant negative strand RNA virus expression–Systems.*

Rauh et al., "Pseudorabies Virus Glycoproteins gII and gp50 Are Essential for Virus Penetration," *Journal of Virology*, 65(10):5348–5356 (1991).

Miner et al., "Anchoring a Vaccinia Virus Promoter in the Nucleus Prevents its Trans–Activation by Viral Infection," *Virus Genes*, 3(4):335–359 (1990).

Moss, B., "Replication of Poxviruses," *Virology*, Ed. B.N. Fields et al., Raven Press:N.Y., pp. 685–703 (1985).

Peeters et al., "Pseudorabies Virus Envelope Glycoproteins gp50 and gII are Essential for Virus Penetration, but only gII is Involved in Membrane Fusion," *Journal of Virology*, 66(2):894–905 (1992).

Ballay, A., et al., "In Vitro in In Vivo Synthesis of the Hepatitis B Virus Surface Antigen and of the Receptor for Polymerized Human Serum Albumin from Recombinant Human Adenoviruses," *The EMBO Journal*, 4(13B):3861–3865 (1985).

Alkhatib, G., et al., "High–Level Eucaryotic In Vivo Expression of Biologically Active Measles Virus Hemagglutinin by Using an Adenovirus Type 5 Helper–Free Vector System," *Journal of Virology*, 61(8):2718–2727 (1988).

Farrell, H.E., et al., "Vaccine Potential of a Herpes Simplex Virus Type 1 Mutant with an Essential Glycoprotein Deleted" *Journal of Virology*, 68(2):927–932 (1994).

(List continued on next page.)

*Primary Examiner*—Mary E. Mosher
(74) *Attorney, Agent, or Firm*—Klarquist Sparkman, LLP

(57) ABSTRACT

A mutant virus for use as a vaccine, wherein the genome of the virus is defective in respect of a gene essential for the production of infectious virus. In one aspect the mutant virus is capable of protecting a susceptible species immunized therewith against infection by the corresponding wild-type virus. In another aspect, the mutant virus acts as a vector for an immunogenic protein derived from a pathogen and which is encoded by foreign DNA incorporated in the mutant virus. The mutant virus can be produced in a recombinant host cell which expresses a gene complementing the defect. The mutant virus is preferably infectious for the host to be protected, but the defective gene allows expression in the infected host of at least some of the viral genes, which can provoke a cell-mediated immune response.

43 Claims, 4 Drawing Sheets

OTHER PUBLICATIONS

Morrison, L.A., et al., "Immunization with Relication–Defective Mutants of Herpes Simplex Virus Type 1: Sites of Immune Intervention in Pathogenesis of Challenge Virus Infection." *Journal of Virology,* 68(2):689–696 (1994).

Peeters, B., et al., "Non–Transmissible Pseudorabies Virus gp50 Mutants: A New Generation of Safe Live Vaccines." *Vaccine,* 12(4):375–380 (1994).

Nguyen L.H., et al., "Replication–Defective Mutants of Herpes Simplex Virus (HSV) Induce Cellular Immunity and Protect Against Lethal HSV Infection." *Journal of Virology,* 66(12):7067–7072 (1992).

Graham, F.L., et al., "Characteristics of a Human Cell Line Transformed by DNA from Human Adenovirus Type 5." *J. Gen. Virol.,* 36:59–72 (1977).

Harrison, T., et al., "Host–Range Mutants of Adenovirus Type 5 Defective for Growth in HeLa Cells." *Virology,* 77:319–329 (1977).

Gluzman, Y., "SV40–Transmformed Simian Cells Support the Replication of Early SV40 Mutants." *Cell,* 23:175–182 (1981).

Cai, W., et al., "Linker–Insertion Nonsense and Restriction–Site Deletion Mutations of the gB Glycoprotein Gene of Herpes Simplex Virus Type 1." *Journal of Virology,* 61(3):714–721 (1987).

Racaniello, V.R., et al., "Cloned Poliovirus Complementary DNA is Infectious in Mammalian Cells." *Science,* 214:916–918 (1981).

Ligas, M.W., et al., "A Herpes Simplex Virus Mutant in which Glycoprotein D Sequences are Replaced by β–Galactosidase Sequences Binds to but is Unable to Penetrate into Cells." *Journal of Virology,* 62(5):1486–1494 (1988).

Fuller, A.O., et al., "Neutralizing Antibodies Specific for Glycoprotein H of Herpes Simplex Virus Permit Viral Attachment to Cells but Prevent Penetration." *Journal of Virology,* 63(8):3435–3443 (1989).

DeLuca, N.A., et al., "Isolation and Characterization of Deletion Mutants of Herpes Simplex Virus Type 1 in the Gene Encoding Immediate–Early Regulatory Protein ICP4." *Journal of Virology,* 56(2):558–570 (1985).

Johnson, D.C., et al., "Herpes Simplex Viruses Lacking Glycoprotein D are Unable to Inhibit Virus Penetration: Quantitative Evidence for Virus–Specific Cell Surface Receptors." *Journal of Virology,* 62(12):4605–4612 (1988).

Desai, P.J., et al., "Excretion of Non–Infectious Virus Particles Lacking Glycoprotein H by a Temperature–Sensitive Mutant of Herpes Simplex Virus Type 1: Evidence that gH is Essential for Virion Infectivity." *J. Gen. Virol.,* 69:1147–1156 (1988).

Luytjes, W., et al., "Amplification, Expression, and Packaging of a Foreign Gene by Influenza Virus." *Cell,* 59:1107–1113 (1989).

Buller, R.M.L., et al., Deletion of the Vaccinia Virus Growth Factor Gene Reduces Virus Virulence, *Journal of Virology,* 62(3):866–874 (1988).

Eliot, M., et al., "Construction of a Defective Adenovirus Vector Expressing the Pseudorabies Virus Glycoprotein gp50 and its Use as a Live Vaccine." *Journal of Gen. Virol.,* 71, 2425–2431 (1990).

Forrester, A., et al., "Construction and Properties of a Mutant of Herpes Simplex Virus Type 1 with Glycoprotein H Coding Sequences Deleted." *Journal of Virology,* 66(1):341–348 (1992).

Ragot, T., et al., "Replication–Defective Recombinant Adenovirus Expressing the Epstein–Barr Virus (EBV) Envelope Glycoprotein gp340/220 Induces Protective Immunity Against EBV–Induced Lymphomas in the Cottontop Tamarin." *Journal of General Virology,* 74:501–507 (1993).

Emi, N., et al., "Pseudotype Formation of Murine Leukemia Virus with the G Protein of Vesicular Stomatitis Virus." *Journal of Virology,* 65(3):1202–1207 (1991).

Dion, M., et al., "Isolation and Preliminary Characterization of Temperature–Sensitive Mutants of Human Cytomegalovirus." *Virology,* 158:228–230 (1987).

McGeoch, D.J., "The Genomes of the Human Herpes Viruses: Contants, Relationships, and Evolution." *Ann. Rev. Microbiol.,* 43:235–265 (1989).

Ensinger, M.J., et al., "Fine Structure Marker Rescue of Temperature–Sensitive Mutations of Vaccinia Virus Within a Central Conserved Region of the Genome." *Journal of Virology,* 56(3):1027–1029 (1985).

Frost, E., et al., "Mapping Temperature–Sensitive and Host–Range Mutations of Adenovirus Type 5 by Marker Rescue." *Virology,* 91:39–50 (1978).

Goeble, S.J., et al., "The Complete DNA Sequence of Vaccinia Virus." *Virology,* 179:247–266 (1990).

Almond, J.W., et al., "Temperature–Sensitive Mutants of Fowl Plague Virus: Isolation and Genetic Characterization." *Virology,* 92:416–427 (1979).

Straus, S.E., et al., "Placebo–Controlled Trial of Vaccination with Recombinant Glycoprotein D of Herpes Simplex Virus Type 2 for Immunotherapy of Genital Herpes." *The Lancet,* 343:1460–1463 (1994).

MeGeoch, D.J., et al., "DNA Sequence of the Herpes Simplex Virus Type I Gene Encoding Glycoprotein gH, and Identification of Homologues in the Genomes of Varicella–Zoster Virus and Epstein–Barr Virus." *Nucleic Acids Research,* 14(10):4281–4292 (1986).

Gao, M., et al., "Genetic Evidence for Multiple Nuclear Functions of the Herpes Simplex Virus ICP8 DNA–Binding Protein." *Journal of Virology,* 63(12):5258–5267 (1989).

McCarthy, A.M., et al., "Herpes Siimplex Virus Type 1 ICP27 Deletion Mutants Exhibit Altered Patterns of Transcription and are DNA Deficient." *Journal of Virology,* 63(1):18–27 (1989).

Ross, L.J.N., et al., "Nucleotide Sequence and Characterization of the Marek's Disease Virus Homologue of Glycoprotein B of Herpes Simplex Virus." *J. Gen. Virol.,* 80:1789–1804 (1989).

Whitbeck, J.C., et al., "Comparison of the Bovine Herpesvirus 1 gI Gene and the Herpes Simplex Virus Type 1 gB Gene." *Journal of Virology,* 62(9):3319–3327 (1988).

Hammerschmidt, W., et al., "Conservation of a Gene Cluster Including Glycoprotein B in Bovine Herpesvirus Type 2 (BHV–2) and Herpes Simplex Virus Type 1 (HSV–2)." *Virology,* 165:388–405 (1988).

Chen, K.C., et al., "Complete Nucleotide Sequence and Genome Organization of Bovine Parvovirus." *Journal of Virology,* 60(3):1085–1097 (1986).

Cotmore, S.F., "Identification of the Major Structural and Nonstructural Proteins Encoded by Human Parvovirus B19 and Mapping of Their Genes by Procaryotic Expression of Isolated Genomic Fragments." *Journal of Virology,* 60(2):548–557 (1986).

Long, D., et al., "Glycoprotein D Protects Mice Against Lethal Challenge with Herpes Simplex Virus Types 1 and 2." *Infection and Immunity,* 43:761–764 (1984).

Straus, S.E., et al., "Induction and Enhancement of Immune Responses to Herpes Simplex Virus Type 2 in Humans by Use of a Recombinant Glycoprotein D Vaccine." *The Journal of Infectious Disease*, 167:1045–1052 (1993).

Pachl, C., et al., "Expression of Cell–Associated and Secreted Forms of Herpes Simplex Virus Type 1 Glycoprotein gB in Mammalian Cells." *Journal of Virology*, 61(2):315–325 (1987).

Ghiasi, H., et al., "Expression of Seven Herpes Simplex Virus Type 1 Glycoproteins (gB, gC, gD, gE, gG, gH, and gI): Comparative Protection Against Lethal Challenge in Mice." *Journal of Virology*, 68(4):2118–2126 (1994).

Garcia, N., "Vaccine Reduces Herpes Outbreaks." *BioWorld Today*, 4(86):1–4 (1993).

Stanberry, L.R., et al., "Genital Herpes in Guinea Pigs: Pathogenesis of the Primary Infection and Description of Recurrent Disease." *The Journal of Infectious Diseases*, 146(3):397–404 (1982).

Cranage, M.P., et al., "Identification and Expression of a Human Cytomegalovirus Glycoprotein with Homology to the Epstein–Barr Virus BXLF2 Product, Varicella–Zoster Virus gpIII, and Herpes Simplex Virus Type 1 Glycoprotein H." *Journal of Virology*, 62(4):1416–1422 (1988).

Mester, J.C., et al., "The Mouse Model and Understanding Immunity to Herpes Simplex Virus." *Reviews of Infectious Diseases*, 13:S935–S945 (1991).

Thomas, G.P., M.B. Mathews, "DNA Replication and the Early to Late Transition in Adenovirus Infection." *Cell*, 22:523–533 (1980).

Fiers, W., et al., "Complete Nucleotide Sequence of SV40 DNA." *Nature*, 273:113–120 (1978).

Somogyi, P., et al., "Fowlpox Virus Host Range Restriction: Gene Expression, DNA Replication, and Morphogenesis in Nonpermissive Mammalian Cells." *Virology*, 197:439–444 (1993).

Perkus, M.E., et al., "Vaccinia Virus Host Range Genes." *Virology*, 179:276–286 (1990).

Tashiro, M., et al., "Cell–Mediated Immunity Induced in Mice after Vaccination with a Protease Activation Mutant, TR–2, of Sendai Virus." *Journal of Virology*, 62:2490–2497 (1988).

Beatrice, S.T., and R.R. Wagner, "Immunigenicity in Mice of Temperature–Sensitive Mutants of Vesicluar Stomatitis Virus: Early Appearance in Bronchial Secretions of an Interferon–Like Inhibitor." *J. Gen. Virol.*, 47:529–533 (1980).

McLaren, L.C. and J.J. Holland, "Defective Interfering Particles from Poliovirus Vaccine and Vaccine Reference Strains." *Virology*, 60:579–583 (1974).

Konishi, E., et al., "A Highly Attenuated Host Range–Restricted Vaccinia Virus Strain, NYVAC, ENcoding the prM, E and NS1 Genes of Japanese Encephalitis Virus Prevents JEV Viremia in Swine." *Virology*, 190:454–458 (1992).

Tartaglia, J., et al., "NYVAC: A Highly Attenuated Strain of Vaccinia Virus." *Virology*, 188:217–232 (1992).

Goodman and Gilman, "The Pharmacologic Basis of Therapeutic" 8th Ed., (1990) pp. 1184–1186.

Akrigg, A., et al., "The Structure of the Major Immediate Early Gene of Human Cytomegalovirus Strain AD169." *Virus Research*, 2:107–121 (1985).

Brierley, I., et al., "Characterization of an Efficient Coronavirus Ribosomal Frameshifting Signal: Requirement for an RNA Pseudoknot." *Cell*, 57:537–547 (1989).

Chakrabarti, L., et al., "Sequence of Simian Immunodeficiency Virus From Macaque and its Relationship to Other Human and Simian Retroviruses." *Nature*, 328(6):543–547 (1987).

Graham, F.L., et al., "A New Technique for the Assay of Infectivity of Human Adenovirus 5 DNA." *Virology*, 52:456–467 (1973).

Chakrabarti, S., et al., "Vaccinia Virus Expression Vector: Coexpression of $\beta$–Galactosidase Provides Visual Screening of Recombinant Virus Plagues." *Molecular and Cellular Biology*, 5(12):3403–3409 (1985).

Everett, R.D., et al., "DNA Sequence Elements Required for Regulated Expression of the HSV–1 Glycoprotein D Gene Lie Within 83 bp of the RNA Capsites." *Nucleic Acids Research*, 11(19):6647–6666 (1983).

Gompels, U.A., et al., "Antigenic Properties and Cellular Localization of Herpes Simplex Virus Glycoprotein H Synthesized in a Mammalian Cell Expression System." *Journal of Virology*, 63(11):4744–4755 (1989).

Krieg, P.A., et al., "Functional Messenger RNAs are Produced by SP6 in vitro Transcription of Cloned cDNAs." *Nucleic Acids Research*, 12(18):7057–7070 (1984).

McGeoch, G.J., et al., "The Complete DNA Sequence of the Long Unique Region in the Genome of Herpes Simplex Virus Type 1." *J. Gen. Virol.*, 69:1531–1574 (1988).

Twigg, A.J., et al., "Trans–Complementable Copy–Number Mutants of Plasmid CoIe1." *Nature*, 283:216–218 (1980).

Vieira, J., et al., "[1] Production of Single–Stranded Plasmid DNA." *Methods in Enzymology*, 143:3–11 (1987).

Hill, T.J., et al., "Acute and Recurrent Infection with Herpes Simplex Virus in the Mouse: a Model for Studying Latency and Recurrent Disease." *J. Gen. Virol.*, 28:341–343 (1975).

Gallichan, W.S., et al., "Mucosal Immunity and Protection after Intranasal Immunization with Recombinant Adenovirus Expressing Herpes Simplex Virus Glycoprotein B." *The Journal of Infectious Diseases*, 168:622–629 (1993).

Stanberry, L.R., et al., "Herpes Simplex Virus Glycoprotein Treatment of Recurrent Genital Herpes," *The Journal of Infectious Diseases*, 157(1):156–163 (1988).

Stanberry, L.R., et al., "Preinfection Prophylaxxis with Herpes Simplex Virus Glycoprotein Immunogens: Factor Influencing Efficacy." *J. Gen. Virol.*, 70:3177–3185 (1989).

Baer, R., et al., "DNA Sequence and Expression of the B95–8 Epstein–Barr Virus Genome." *Nature*, 310:207–211 (1984).

Killington, R.A., et al., "Growth, Assay and Purification of Herpesviruses." *Techniques in Virology*, 207–236 (1994).

\* cited by examiner

Fig.3a.
5' GATCCACCATGACCATGATTA
           GTGGTACTGGTACTAATCTAG 5'
Fig.3b.
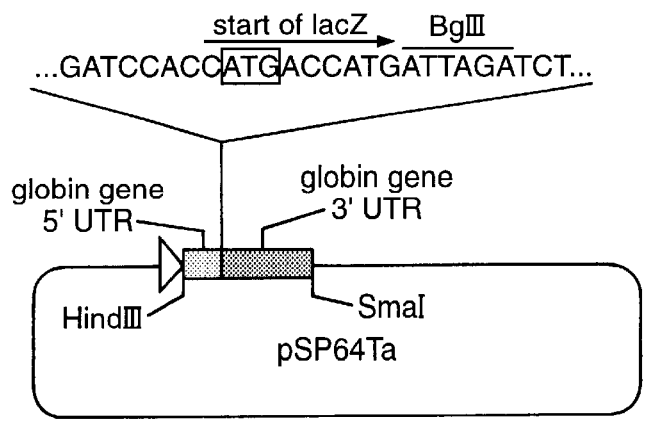
Fig.4a.
Upstream Primer
        HindIII   SmaI        CMV sequence
5' ATCAAGCTTCCCGGGCCTGGCATTATGCCCAGTACATG
Downstream primer
        HindIII      CMV sequence
5' TCAAAGCTTGAGCTCTGATTATATAGACCTCCC
Fig.4b.
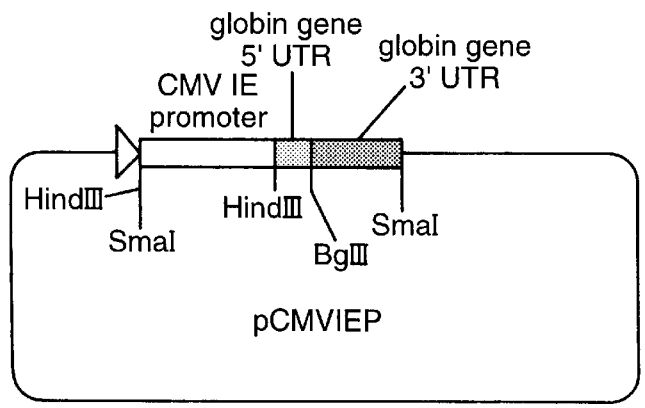

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: complement (5..21)
        (D) OTHER INFORMATION: /note= "Complementary to SEQ ID
            NO:2, bases 5 to 21."

(xi) SEQUENCE DESCRIPTION: SEQ ID NO:1:

GATCCACCAT GACCATGATT A                                              21

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: complement (5..21)
        (D) OTHER INFORMATION: /note= "Complementary to SEQ ID NO:1, bases 21 to 5."

(xi) SEQUENCE DESCRIPTION: SEQ ID NO:2:

GATCTAATCA TGGTCATGGT G                                                    21

(2) INFORMATION FOR SEQ ID NO:3:

(i) SEQUENCE CHARACTERISTICS:
      (A) LENGTH: 26 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: misc_RNA
      (B) LOCATION: 9
      (D) OTHER INFORMATION: /note= "Start of lacZ."

(ix) FEATURE:
      (A) NAME/KEY: misc_feature
      (B) LOCATION: complement (18..23)
      (D) OTHER INFORMATION: /note= "BglII restriction site."

(xi) SEQUENCE DESCRIPTION: SEQ ID NO:3:

GATCCACCAT GACCATGATT AGATCT                                               26

(2) INFORMATION FOR SEQ ID NO:4:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 5..10
      (D) OTHER INFORMATION: /note= "HindIII restriction site."

(ix) FEATURE:
      (A) NAME/KEY: misc_feature
      (B) LOCATION: 10..15
      (D) OTHER INFORMATION: /note= "SmaI restriction site."

(ix) FEATURE:
      (A) NAME/KEY: misc_feature
      (B) LOCATION: 16..38
      (D) OTHER INFORMATION: /note= "CMV sequence."

(xi) SEQUENCE DESCRIPTION: SEQ ID NO:4:

ATCAAGCTTC CCGGGCCTGG CATTATGCCC AGTACATG                                  38

(2) INFORMATION FOR SEQ ID NO:5:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 4..9
      (D) OTHER INFORMATION: /note= "HindIII restriciton site."

(ix) FEATURE:
      (A) NAME/KEY: misc_feature (B) LOCATION: 11..33
        (D) OTHER INFORMATION: /note= "CMV sequence."

(xi) SEQUENCE DESCRIPTION: SEQ ID NO:5:

TCAAAGCTTG AGCTCTGATT ATATAGACCT CCC                             33

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 9..14
        (D) OTHER INFORMATION: /note= "EcoRV restriction site."

(xi) SEQUENCE DESCRIPTION: SEQ ID NO:6:

GAAGAAGGCT ATAGCTAATA CAT                                        23

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CAAGAAATAA ACTATAGGTC TTTGTGC                                    27

(2) INFORMATION FOR SEQ ID NO:8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 4..9
        (D) OTHER INFORMATION: /note= "EcoRI restriction site."

(ix) FEATURE:
        (A) NAME/KEY: misc_feature
        (B) LOCATION: 10..15
        (D) OTHER INFORMATION: /note= "EcoRV restriction site."

(xi) SEQUENCE DESCRIPTION: SEQ ID NO:8:

ATCGAATTCC TATAGCCTGG CATTATGCCC AGTACATG                        38

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (ix) FEATURE:

```
        (A) NAME/KEY: misc_feature
        (B) LOCATION: 4..9
        (D) OTHER INFORMATION: /note= "HindIII restriction site."

(ix) FEATURE:
        (A) NAME/KEY: misc_feature
        (B) LOCATION: 10..15
        (D) OTHER INFORMATION: /note= "EcoRV restriction site."

(ix) FEATURE:
        (A) NAME/KEY: misc_feature
        (B) LOCATION: 16..21
        (D) OTHER INFORMATION: /note= "SmaI restriction site."

(xi) SEQUENCE DESCRIPTION: SEQ ID NO:9:

TCAAAGCTTC TATAGCCCGG GGAGCTCTGA TTATATAGAC CTCCC                      45
```

VIRAL VACCINES

This is a division of application Ser. No. 08/384,963 filed Feb. 7, 1995 now U.S. Pat. No. 5,665,362 which is a continuation of application Ser. No. 08/030,073 filed on May 20, 1993, now abandoned.

Said application Ser. No. 08/030,073 is the national phase entry application from International application PCT/GB91/01632, filed Sep. 23, 1991, which is based on Great Britain Application Nos. 9020799.4 filed Sep. 25, 1990 and 9104903 filed Mar. 8, 1991.

The present invention relates to viral vaccines. In particular, it relates to genetically engineered mutant viruses for use as vaccines; vaccines comprising the mutant viruses; recombinant cell; and to methods relating to the production of vaccines.

Viral vaccines are traditionally of two sorts. The first sort are 'killed' vaccines, which are virus preparations which have been killed by treatment with a suitable chemical such as beta-propiolactone. The second type are live 'attenuated' vaccines, which are viruses which have been rendered less pathogenic to the host, either by specific genetic manipulation of the virus genome, or, more usually, by passage in some type of tissue culture system. These two types of vaccine each have their own disadvantages. Since killed vaccines do not replicate in the host, they must be administered by injection, and hence may generate an inappropriate kind of immune response. For example the Salk vaccine, a killed preparation of poliovirus, produces an immunoglobulin (Ig) G antibody response, but does not stimulate the production of IgA in the gut, the natural site of primary infection. Hence this vaccine, though it can protect the individual from the neurological complications of poliomyelitis, does not block primary infection, and so does not confer "herd immunity". In addition, killed viruses, do not enter and replicate inside host cells. Hence any beneficial immunological response to non-structural proteins produced during replication is not available. They also cannot stimulate the production of cytotoxic T cells directed against virus antigens. "Dead" antigens can be picked up by antigen presenting cells and presented to T cells. However, the presentation occurs via MHC Class II molecules and leads to stimulation of T helper cells. In turn, the T helper cells help B cells to produce specific antibody against the antigen. In order to stimulate the production of cytotoxic T cells, virus antigens must be processed through a particular pathway inside the infected cell, and presented as broken-up peptide fragments on MHC Class I molecules. This degradation pathway is thought to work most effectively for proteins that are synthesised inside the infected cell, and hence only virus that enters host cells and expresses immunogenic viral protein is capable of generating virus-specific cytotoxic T cells. Therefore, killed vaccines are poor inducers of cellular immunity against virus infection. From this point of view, live attenuated vaccines are more satisfactory.

To date, live attenuated viruses have been made by deleting an inessential gene or partly damaging one or more essential genes (in which case, the damage is such that the genes are still functional, but do not operate so effectively). However, live attenuated viruses often retain residual pathogenicity which can have a deleterious effect on the host. In addition, unless the attenuation is caused by a specific deletion, there remains the possibility of reversion to a more virulent form. Nevertheless, the fact that some viral protein production occurs in the host means that they are often more effective than killed vaccines which cannot produce such viral protein.

Live attenuated viruses, as well as being used as vaccines in their own right, can also be used as 'vaccine vectors' for other genes, in other words carriers of genes from a second virus (or other pathogen) against which protection is required. Typically, members of the pox virus family eg. vaccinia virus, are used as vaccine vectors. When a virus, is used as a vaccine vector, it is important that it causes no pathogenic effects. In other words it may need to be attenuated in the same way that a simple virus vaccine is attenuated. The same disadvantages as those described above, therefore apply in this case.

It has been found possible to delete a gene from a viral genome and provide a so-called 'complementing' cell which provides the virus with the product of the deleted gene. This has been achieved for certain viruses, for example adenoviruses, herpesviruses and retroviruses. For adenoviruses, a human cell line was transformed with fragments of adenovirus type 5 DNA (Graham, Smiley, Russell & Nairn, J. Gen. Virol., 36,59–72, 1977). The cell line expressed certain viral genes, and it was found that it could support the growth of virus mutants which had those genes deleted or inactivated (Harrison, Graham & Williams, Virology 77, 319–329, 1977). Although the virus grew well on this cell line (the 'complementing cell line') and produced standard viral particles, it could not grow at all on normal human cells. Cells expressing the T-antigen-encoding region of the SV40 virus genome (a papovavirus) have also been shown capable of supporting the replication of viruses specifically deleted in this region (Gluzman, Cell, 23,182–195, 1981). For herpes simplex virus, cell lines expressing the gB glycoprotein (Cai et al, J. Virol. 62,714–721, 1987) the gD glycoprotein (Ligas and Johnson, J. Virol. 62,1486, 1988) and the Immediate Early protein ICP4 (Deluca et al., J. Virol., 56,558, 1985) have been produced, and these have been shown capable of supporting the replication of viruses with specifically inactivated copies of the corresponding genes.

The present invention provides a mutant virus for use as a vaccine, in which a viral gene encoding a protein which is essential for the production of infectious virus has been deleted or inactivated; and wherein said virus can be grown in a cell which has a heterologous nucleotide sequence which allows said cell to express the essential protein encoded by said deleted or inactivated viral gene.

The present invention also provides a vaccine which comprises a virus as described above, together with one or more excipients and/or adjuvants. The viral genome may itself provide the immunogen, or it may contain a heterologous gene insert expressing the immunogenic protein.

The present invention also provides a complementing cell transfected with an attenuated virus as described above, for use in the preparation of a vaccine.

The present invention also provides a method which comprises the use of a virus as described above in the preparation of a vaccine for the therapeutic or prophylactic treatment of a disease.

The present invention also provides a method for the production of a vaccine which comprises: culturing a cell infected with a virus having a deleted or inactivated viral gene encoding a protein which is essential for the production of infectious virus, and wherein the host cell has a heterologous nucleotide sequence comprising said viral gene and which is able to express the essential protein encoded by said gene; harvesting the virus thus produced, and using it in a vaccine.

The virus may be derived from herpes simplex virus (HSV) in which, for example, the gene encoding glycoprotein H (gH) has been inactivated or deleted. The mutant virus may also comprise a heterologous sequence encoding an immunogen derived from a pathogen. The host cell will suitably be a recombinant eukaryotic cell line containing the gene encoding HSV glycoprotein H. As another example the virus may be derived from an orthopox virus, for example, vaccinia virus, which again may comprise a heterologous sequence encoding an immunogen derived from a pathogen.

This invention shows a unique way of combining the efficacy and safety of a killed vaccine with the extra immunological response induced by the in vivo production of viral protein by the attenuated vaccine. In preferred embodiments it comprises two features. Firstly, a selected gene is inactivated within the virus genome, usually by creating a specific deletion. This gene will be involved in the production of infectious virus, but preferably not preventing replication of the viral genome. Thus the infected cell can produce more viral protein from the replicated genetic material, and in some cases new virus particles may be produced, but these would not be infectious. This means that the viral infection cannot spread from the site of inoculation.

A second feature of the invention is a cell which provides the virus with the product of the deleted gene, thus making it possible to grow the virus in tissue culture. Hence, although the virus lacks a gene encoding an essential protein, if it is grown in the appropriate host cell, it will multiply and produce complete virus particles which are to outward appearances indistinguishable from the original virus. This mutant virus preparation is inactive in the sense that it has a defective genome and cannot produce infectious virus in a normal host, and so may be administered safely in the quantity required to generate directly a humoral response in the host. Thus, the mutant virus need not be infectious for the cells of the host to be protected and merely operates in much the same way as a conventional killed or attenuated virus vaccine. However, preferably the immunising virus is itself still infectious, in the sense that it can bind to a cell, enter it, and initiate the viral replication cycle and is therefore capable of initiating an infection within a host cell of the species to be protected, and producing therein some virus antigen. There is thus the additional opportunity to stimulate the cellular arm of the host immune system.

The deleted or inactivated gene is preferably one involved as late as possible in the viral cycle, so as to provide as many viral proteins as possible in vivo for generating an immunogenic response. For example, the gene may be one involved in packaging or some other postreplicative event, such as the gH glycoprotein of HSV. However, the selected gene may be one involved in the viral genome replication, and the range of proteins expressed in vivo will depend upon the stage at which that gene is normally expressed. In the case of human cytomegalovirus (HCMV) the selected gene may be one (other than the Immediate Early gene) that effectively prevents viral genome replication in vivo, since the Immediate Early gene which is produced prior to viral genome replication (and indeed is essential for it) is highly immunogenic.

This invention can be applied to any virus where one or more essential gene(s) can be identified and deleted from or inactivated within the virus genome. For DNA viruses, such as Adeno, Herpes, Papova, Papilloma and Parvo viruses, this can be achieved directly by (i) the in vitro manipulation of cloned DNA copies of the selected essential gene to create specific DNA changes; and (ii) re-introduction of the altered version into the virus genome through standard procedures of recombination and marker rescue. The invention however, is also applicable to RNA viruses. Techniques are now available which allow complementary DNA copies of a RNA virus genome to be manipulated in vitro by standard genetic techniques, and then converted to RNA by in vitro transcription. The resulting RNAs may then be re-introduced into the virus genome. The technique has been used to create specific changes in the genome of both positive and negative stranded RNA viruses, e.g. poliovirus (Racaniello and Baltimore, Science, 214, 916–919, 1981) and influenza virus (Lutyes et al., Cell, 59, 1107–1113, 1989).

In theory, any gene encoding an essential protein should be a potential target for this approach to the creation of attenuated viruses. In practice however, the selection of the gene will be driven by a number of considerations.

1. The gene should preferably be one which is required later in infection. Thus replication of the attenuated virus is not interrupted in the early phase. This means that most and possibly all other virus antigens will be produced in the infected cell, and presented to the host immune system in conjunction with host cell MHC class 1 molecules. Such presentation leads to the development of cellular immunity against virus infection through the production of cytotoxic T cells. The cytotoxic T cells can recognise these antigens, and therefore kill virus infected cells. It is possible that the deleted gene could represent one which is not required at all for virus assembly, but is necessary for the assembled virus to be able to infect new cells. An example of such a protein is the HSV gH protein. In the absence of this protein, HSV virions are still produced, but they are non-infectious.

2. Ideally, the product of the selected gene should not, on its own, be toxic to the eukaryotic cell, so that a complementing cell can be produced relatively easily. This however is not an absolute requirement, since the gene may be placed under the control of an inducible promoter in the complementing cell, such that its expression may be switched on only when required.

The nature of the mutation created in the target gene is also a matter of choice. Any change which produces a non-functional gene product is satisfactory, as long as the risk of reversion to a wild type structure is minimised. Such changes include interruption of the target with extraneous sequences and creation of specific deletions. The most satisfactory strategy for a vaccine to be used as a therapeutic and/or prophylactic however, would be one where a deletion is made that encompasses the entire sequence to be introduced into the complementing cell. The approach minimises the risk of regenerating wild type virus through recombination between the virus and cell DNA in the complementing cell.

Although there are several examples of combinations of specifically inactivated viruses and complementing cells, (see earlier discussion), to date, these have been used either for basic research on the virus, or, as in the case of retroviruses, to make a safer vector for producing transgenic animals. They have not been used for vaccine purposes, and to the applicants knowledge no suggestion of this kind of use has been proposed.

As well as using such an inactivated virus/complementing cell combination to produce safe vaccines against the wild-type virus, this invention also deals with the use of the same system to produce safe viral vectors for use as vaccines against foreign pathogens.

An example of such a vector is one based on HSV. The HSV genome is large enough to accommodate considerable additional genetic information and several examples of recombinant HSV viruses carrying and expressing foreign genetic material have been described (e.g. Ligas and Johnson, J. Virol. 1988, op. cit.). Thus a virus with a deletion in an essential virus gene as described above, and also carrying and expressing a defined foreign gene, could be used as a safe vector for vaccination to generate an immune response against the foreign protein.

A particular characteristic of HSV is that it may become latent in neurones of infected individuals, and occasionally reactivate leading to a local lesion. Thus an HSV with a deletion in an essential virus gene and expressing a foreign gene could be used to produce deliberately latent infection of neurones in the treated individual. Reactivation of such a latent infection would not lead to the production of a lesion, since the virus vector would be unable to replicate fully, but would result in the onset of the initial part of the virus replication cycle. During this time expression of the foreign antigen could occur, leading to the generation of immune response. In a situation where the deleted HSV gene specified a protein which was not needed for virus assembly, but only for infectivity of assembled virions, such a foreign antigen might be incorporated into the assembled virus particles, leading to enhancement of its immunogenic effect. This expression of the foreign gene and incorporation of its protein in a viral particle could of course also occur at the stage where the mutant virus is first produced in its complementing host, in which case the mutant virus when used as a vaccine could present immediately the foreign protein to the species being treated.

In another example, vaccinia virus, a poxvirus, can carry and express genes from various pathogens, and it has been demonstrated that these form effective vaccines when used in animal experimental systems. The potential for use in humans is vast, but because of the known side effects associated with the widespread use of vaccinia as a vaccine against smallpox, there is reluctance to use an unmodified vaccinia virus on a large scale in humans. There have been attempts to attenuate vaccinia virus by deleting non-essential genes such as the vaccinia growth factor gene (Buller, Chakrabarti, Cooper, Twardzik & Moss, J. Virology 62,866–874, 1988). However, such attenuated viruses can still replicate in vivo, albeit at a reduced level. No vaccinia virus with a deletion in an essential gene has yet been produced, but such a virus, deleted in an essential gene as described above, with its complementing cell for growth, would provide a safer version of this vaccine vector.

A further advantage of this general strategy for immunisation against heterologous proteins is that it may be possible to perform multiple effective vaccinations with the same virus vector in a way not possible with conventional live virus vectors. Since a standard live virus vaccine probably relies for its efficacy on its ability to replicate in the host animal through many cycles of infection, its usefulness will be severely curtailed in an individual with immunity against that virus. Thus a second challenge with the same virus, whether to provide a booster immunisation against the same protein, or a new response against a different protein, is likely to be ineffective. Using a virus vector with a deletion in an essential gene however, where multi-cycle replication is not desired or required, the events leading to effective immunisation will occur very soon after immunisation. The dose of the mutant virus can be relatively large (since it should be completely safe), and it is therefore unlikely that these early events will be blocked by the host immune response, which will require some time to be mobilised completely.

Although we have referred above to a mutant virus being defective in an essential gene, and optionally containing a gene for an immunogenic pathogen protein, the mutant could be defective in more than one essential gene, and/or contain more than one immunogenic pathogen protein gene. Thus, the mutant virus might include the gene for HIV gp 120, to act as a vaccine in the manner suggested above, and also the gene for the HIV gag protein to be expressed within the vaccinated host and presented at the surface of the host cell in conjunction with MHC-I to stimulate a T-cell response in the host.

In order that the invention is more clearly understood, it will be further described by way of example only, and not by way of limitation, with reference to the following figures in which:

FIG. 3a shows the pair of complementary oligonucleotides (SEQ ID NO:1, SEQ ID NO:2) used to generate the plasmid pSP64Ta;

FIG. 3b illustrates the production of plasmid pSP64TA;

FIG. 4a shows the two oligonucleotides (SEQ ID NO:4, SEQ ID NO:5) used to generate the plasmid pCMVIEP;

FIG. 4b illustrates the plasmid pCMVIEP;

Herpes Simplex Virus Deleted in Glycoprotein H (gH-HSV)

Herpes simplex virus (HSV) is a large DNA virus which causes a wide range of pathogenic symptoms in man, including recurrent facial and genital lesions, and a rare though often fatal encephalitis. Infection with this virus can be controlled to some extent by chemotherapy using the drug Acyclovir, but as yet there is no vaccine available to prevent primary infection. A difficulty with vaccination against HSV is that the virus generally spreads within the body by direct transfer from cell to cell. Thus humoral immunity is unlikely to be effective, since circulating antibody can only neutralise extracellular virus. Of more importance for the control of virus infection, is cellular immunity, and so a vaccine which is capable of generating both humoral and cellular immunity, but which is also safe, would be a considerable advantage.

A suitable target gene for inactivation within the HSV genome is the glycoprotein H gene (gH). The gH protein is a glycoprotein which is present on the surface of the virus envelope. This protein is thought to be involved in the process of membrane fusion during entry of the virus into the infected cell. This is because temperature sensitive virus mutants with a lesion in this gene are not excreted from virus infected cells at the non-permissive temperature (Desai et al., J. Gen. Virol. 69, 1147–1156, 1988). The protein is expressed late in infection, and so in its absence, a considerable amount of virus protein synthesis may still occur.

All genetic manipulation procedures are carried out according to standard methods described in "Molecular Cloning", A Laboratory Manual, eds. Sambrook, Fritsch and Maniatis, Cold Spring Harbor Laboratory Press, 1989.

A. Generation of a Cell Line Expressing the HSV gH Gene

The gH gene is present in the Unique Long region ($U_L$) of the HSV type 1 genome, between nucleotides 46382 and 43868 (McGeoch et al, J. Gen. Virol. 69, 1531–1574, 1988). A cloned copy of this gene is available within the plasmid pAF2. This plasmid was produced by excising a BglII-XhoI fragment, encompassing the complete gH coding sequence, from the plasmid pTZgH, and cloning it into the BglII site of plasmid pSP64T as described (Gompels and Minson, J.

Figure 1:
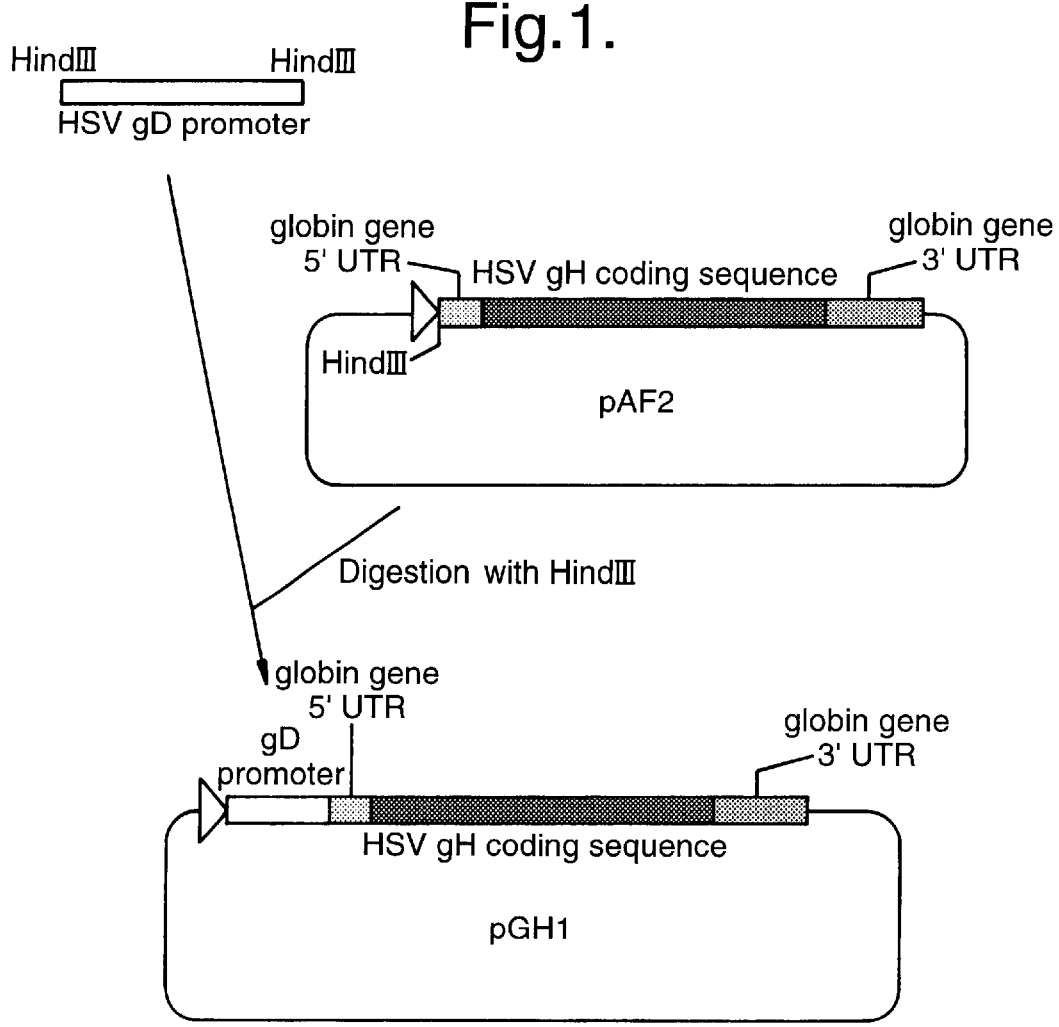
FIG. 1 illustrates the production of plasmid pGH1.

Virol., 63, 4744–4755, 1989). A HindIII fragment containing the promoter sequence for the glycoprotein D (gD) gene (extending from nucleotides −392 to +11, with respect to the start of the gD gene) is then excised from the plasmid pSVD4 (Everett, Nucl. Acids Res., 11, 6647–6667, 1983), and cloned into the unique HindIII site of pAF2 to generate pGH1 (FIG. 1) such that the promoter sequence is in the correct orientation to drive expression of the gH gene. Thus this plasmid contains the complete gH coding sequence under the control of the HSV type 1 gD gene promoter. This plasmid is then purified and then co-transfected into Vero cells with the plasmid pNEO (Pharmacia LKB Biotechnology Inc.) using the standard calcium phosphate co-precipitation technique (Graham and Van der Eb, Virology 52, 456–467, 1973). Vero cells which have acquired resistance to neomycin are then selected by passage of the cells in the drug G418, and colonies of these cells cloned by limiting dilution. These neomycin resistant cells are then amplified in tissue culture, and samples are then infected with HSV type 2 virus. Infection with the HSV type 2 virus has the effect of inducing transcription from the type 1 gD promoter present in the complementing cell genome, and so of stimulating production of the type 1 gH protein in the complementing cell. Lysates of the infected cells are then screened for expression of the gH protein by western blotting, using a polyclonal antiserum known to recognise specifically the type 1 gH protein (Desai et al., 1988 op cit.). Cells which express the required protein are then retained and frozen stocks prepared. This material represents the gH+ complementing cell line.

B. Production of HSV Type 1 Virus with an Interrupted gH Gene

Figure 2:
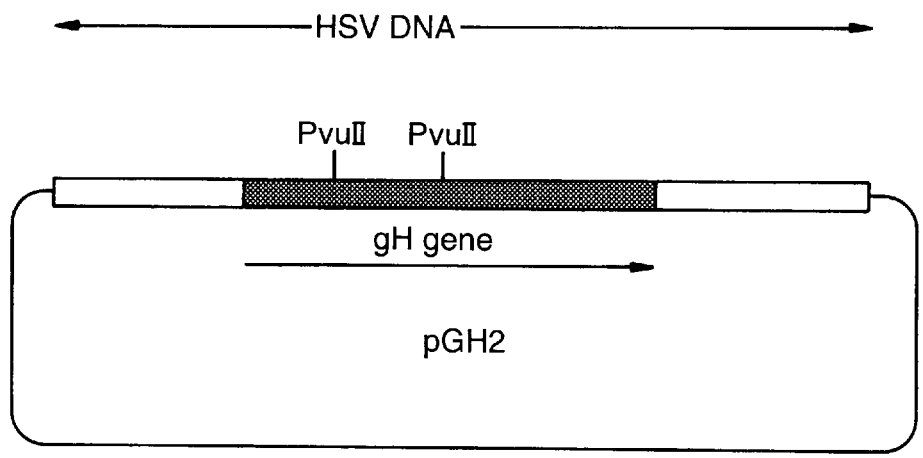
FIG. 2 illustrates the production of plasmid pGH2.
Figure 5:
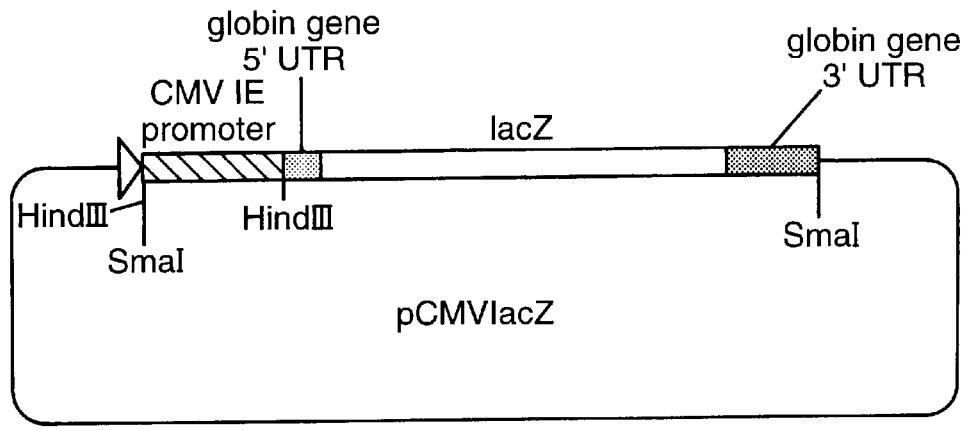
FIG. 5 illustrates the plasmid pCMVlacZ.
Figure 6:
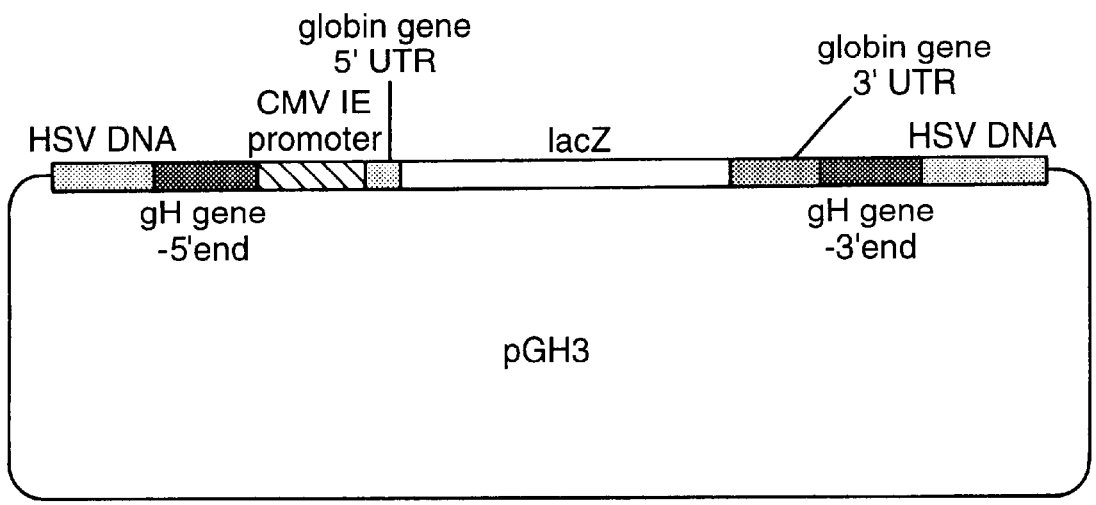
FIG. 6 illustrates the plasmid pGH3.

A 6432 base pair BglII fragment containing the coding sequence of gH together with HSV flanking sequences is excised from the plasmid pUG102 (Gompels and Minson, Virology 153, 230–247, 1986) and cloned into the plasmid pAT153 (Twigg and Sherrat, Nature, 283,216, 1980) to generate pGH2 (FIG. 2). This plasmid is digested with PvuII which cuts only within the gH coding sequence at two positions (nucleotides 44955 and 46065 according to the numbering scheme of McGeoch et al, 1988, op cit.), and the larger of the two fragments purified. A fragment of DNA consisting of the complete B-galactosidase gene from E coli downstream of the Immediate Early gene promoter from Cytomegalovirus (CMV) is then prepared by the following procedure. First of all a pair of complementary oligonucleotides (SEQ ID NO:1, SEQ ID NO:2) (shown in FIG. 3a) are annealed and ligated with BglII-digested, phosphatase-treated pSP64T (Krieg and Melton, Nucl. Acids Res. 12, 7057–7071, 1984) to generate the plasmid pSP64Ta as shown in FIG. 3b (SEQ ID NO:3). The added linker (SEQ ID NO:3) also includes the initiation codon and first three codons of the B-galactosidase gene (lacZ) of E.coli. Next the "core region" of the Immediate Early gene promoter of CMV is amplified from plasmid pUG-H1 (Gompels and Minson, 1989, op cit.) by the Polymerase Chain Reaction technique (PCR-Molecular Cloning, ed. Sambrook et al., op cit.) using the two oligonucleotides shown in FIG. 4a, which correspond to sequences from −302 to −288 (SEQ ID NO:4), and from −13 to −36 (SEQ ID NO:5) respectively (numbered in relation to the start of the CMV Immediate Early gene as described by Akrigg et al., Virus Research, 2, 107–121, 1985). These oligonucleotides (SEQ ID NO:1, SEQ ID NO:2) also contain, at their 5' ends, sites for the restriction enzyme HindIII, and in the case of the oligonucleotide annealing upstream of the promoter (SEQ ID NO:4), an additional SmaI site. The PCR-amplified product DNA is then digested with HindIII, and cloned into HindIII-digested pSP64Ta, to generate the plasmid pCMVIEP (FIG. 4b). Finally, a DNA fragment containing a complete copy of the E.coli B-galactosidase gene, lacking only the extreme 5' end of the coding sequence, is isolated by digestion of the plasmid pSC8 (Chakrabarti et al., Mol. Cell. Biol.,5, 3403–3409, 1985) with BamHI, and cloned into the unique BglII site of pCMVIEP to generate pCMVlacZ (FIG. 5). A fragment of DNA containing the B-galactosidase gene under the control of the CMV IE promoter is then isolated by digestion of pCMVIacZ with SmaI, and ligated with the purified PvuII fragment of pGH2 described above, to generate pGH3, which consists of a copy of the gH gene interrupted by a functional B-galactosidase gene (FIG. 6). The next step is to replace the wild type gH gene in the HSV genome with this interrupted version, and this is done by allowing recombination between HSV DNA and plasmid pGH3, followed by selection of those viruses which have acquired a functional B-galactosidase gene. Plasmid pGH3 DNA is therefore cotransfected into cells expressing the gH gene (the gH+ complementing cell line described in section A) along with purified HSV DNA isolated from purified HSV virions (Killington and Powell, In "Techniques in Virology: A practical Approach" (ed. B. W. J. Mahy) pp. 207–236, IRL Press, Oxford (1985)) by the standard calcium phosphate precipitation technique (Graham and Van der Eb, 1973, op cit.) The progeny HSV virus produced from this transfection experiment is then plated on monolayers of gH+ complementing cells by standard plaque assay, using an agar overlay, in the presence of 5-bromo-chloro-3-indolyl-β-D-galactoside (X-gal), a chromogenic substrate which is converted to a blue substance by the enzyme β-galactosidase. Thus plaques resulting from infection by virus genomes containing and expressing the B-galactosidase gene will appear blue. These virus genomes should therefore carry an interrupted version of the gH gene. Virus is recovered from these plaques by picking plugs of agar from the appropriate part of the plate, and virus stocks prepared through growth of virus in the gH+ complementing cell line. These viruses, since they bear non-functional versions of the gH gene, should be unable to form plaques on cells which do not contain and express an endogenous functional copy of the gH gene, and so to confirm this, a sample of the virus is assayed for its ability to form plaques on wild type Vero cell monolayers in comparison with the gH-complementing cells. Finally, virus DNA is prepared from these stocks, and checked for the expected DNA structure around the gH gene by Southern blotting. After confirmation of the correct genetic structure, a large stock of the gH gene-deficient virus is then prepared by inoculation of a sample of the virus into a large-scale culture of the gH+ complementing cell line (multiplicity of infection=0.01), and three days later, the infected cells are harvested. The infected cells are disrupted by sonication in order to release the cell-associated virus, and the total sonicated mixture stored at −70° as the virus master stock. The titre of the virus stock is then established by plaque assay on the gH+ complementing cell line. Samples of this virus stock are then used to prepare working stocks as before, and these working stocks are then used to infect laboratory animals as described below.

C. Studies on the Protective Effect of gH-HSV Compared to Heat Killed Virus

In order to assess the host immunological response to this virus, challenge experiments were conducted in mice according to the experimental plan described below.

The protective effect of a live gH⁻ virus preparation was compared with an inactivated preparation of wild type (WT) virus (strain SC16) as follows.

Preparation of Inactivated Wild Type Virus for Vaccination

HSV type 1 (strain SC16) was grown by low multiplicity infection (0.01 pfu/cell) of Vero cells. After three days, the virus was harvested, and cytoplasmic virus recovered by Dounce homogenisation. Nuclei were removed by centrifugation at 500×g for 15 min, and the virus was recovered from the supernatant by centrifugation on to a 40% sucrose cushion at 12 K for 60 min Beckman Sw27 rotor. The banded virus was diluted, pelleted and purified by sucrose gradient centrifugation (Killington and Powell, 1985, op cit.). The virus band was harvested from the gradient, and the virus recovered by centrifugation. Virus was resuspended in phosphate-buffered saline (PBS), assayed for infectivity by plaque titration on baby hamster kidney (BHK) cells, and the particle count determined by electron microscopy. The particle:infectivity ratio of the preparation was 110 particles/pfu. The virus was diluted to $2.5 \times 10^{10}$ pfu/ml in PBS, and inactivated by treatment with βpropiolactone for 60 min at 20° C. Aliquots were then stored at −70° C.

Preparation of Live gH⁻ Virus for Vaccination

This material was prepared as described for the wild type virus, except that the virus was grown in the gH+ complementing cell line containing and expressing the HSV type 1 gH gene, and it was not inactivated by treatment with β-propiolactone. The particle: infectivity ratio of this preparation was 150:1. The concentration of this preparation was adjusted to $2.5 \times 10^{10}$ pfu/ml, and aliquots were stored in PBS at −70° C.

Vaccination Protocol 4 week-old female balb/C mice (purchased from Tucks U.K. Ltd) were vaccinated with various doses of inactivated WT virus or live gH− virus in 2 μl volumes of phosphate-buffered saline by droplet application and needle scarification of the right ear as follows:

| | |
|---|---|
| Group A | Control - no virus |
| Group B | $5 \times 10^4$ pfu virus vaccine |
| Group C | $5 \times 10^5$ pfu virus vaccine |
| Group D | $5 \times 10^6$ pfu virus vaccine |
| Group E | $5 \times 10^7$ pfu virus vaccine |

After 14 days, all mice were challenged by similar inoculation of the left ear with $2 \times 10^6$ pfu HSV-1 strain SC16 (wild type virus). Mice were killed after 5 days and assayed for virus infectivity in the left ear and left cervical ganglia cII, cIII and cIV (combined). For latency studies, other vaccinated and challenged animals were killed after 1 month, and tested for latent infection by dissecting out the cII, cIII and cIV ganglia. These were incubated in medium for five days then homogenised and assayed for the presence of infectious virus by standard plaque assay. All the following results are expressed as pfu/organ.

TABLE 1

Titre of challenge virus present during the acute phase of infection after vaccination with live gH- virus

| | Mouse no. | Ears | mean | cervical ganglia* | mean |
|---|---|---|---|---|---|
| group A | 1 | 4.2 | 4.3 | 3.3 | 3.4 |
| | 2 | 4.2 | | 3.4 | |
| | 3 | 4.6 | | 3.4 | |
| | 4 | 4.3 | | 3.4 | |

TABLE 1-continued

Titre of challenge virus present during the acute phase of infection after vaccination with live gH- virus

| | Mouse no. | Ears | mean | cervical ganglia* | mean |
|---|---|---|---|---|---|
| group B | 1 | 3.4 | 0.85 | 1.5 | 1.8 |
| | 2 | none | | 2.4 | |
| | 3 | none | | 2.0 | |
| | 4 | none | | 1.5 | |
| group C | 1 | none | — | none | — |
| | 2 | none | | none | |
| | 3 | none | | none | |
| | 4 | none | | none | |
| group D | 1 | none | — | none | — |
| | 2 | none | | none | |
| | 3 | none | | none | |
| | 4 | none | | none | |
| group E | 1 | none | — | none | — |
| | 2 | none | | none | |
| | 3 | none | | none | |
| | 4 | none | | none | |

*Pooled cervical ganglia cII, cIII and cIV

TABLE 2

Titre of challenge virus present during the acute phase of infection after vaccination with inactivated WT HSV-1

| | Mouse no. | Ears | mean | cervical ganglia* | mean |
|---|---|---|---|---|---|
| group A | 1 | 5.7 | 5.2 | 2.6 | 2.3 |
| | 2 | 4.4 | | 2.3 | |
| | 3 | 5.7 | | 2.1 | |
| group B | 1 | 4.2 | 3.8 | 1.9 | 1.2 |
| | 2 | 3.6 | | 3.1 | |
| | 3 | 3.5 | | none | |
| | 4 | 3.8 | | none | |
| group C | 1 | none | 2.0 | none | — |
| | 2 | 2.5 | | none | |
| | 3 | 2.9 | | none | |
| | 4 | 2.7 | | none | |
| group D | 1 | 3.9 | 2.6 | none | — |
| | 2 | 2.0 | | none | |
| | 3 | 2.0 | | none | |
| | 4 | 2.3 | | none | |
| group E | 1 | none | — | none | — |
| | 2 | none | | none | |
| | 3 | none | | none | |
| | 4 | none | | none | |

*Pooled cervical ganglia cII, cIII and cIV

TABLE 3

Titre of challenge virus present as latent virus in the cervical ganglia after vaccination with live gH- HSV-1

| | Mouse no. | Virus titre in-cervical ganglia* ($\log_{10}$pfu WT) | reactivation frequency |
|---|---|---|---|
| group A | 1 | 5.4 | 5/5 |
| | 2 | 4.6 | |
| | 3 | 5.0 | |
| | 4 | 4.8 | |
| | 5 | 5.3 | |
| group B | 1 | none | 3/4 |
| | 2 | 1.5 | |
| | 3 | 5.1 | |

TABLE 3-continued

Titre of challenge virus present as latent virus in the cervical ganglia after vaccination with live gH-HSV-1

| | Mouse no. | Virus titre in-cervical ganglia* ($\log_{10}$pfu WT) | reactivation frequency |
|---|---|---|---|
| | 4 | 5.3 | |
| group C | 1 | none | 1/3 |
| | 2 | none | |
| | 3 | 3.2 | |
| group D | 1 | none | 0/4 |
| | 2 | none | |
| | 3 | none | |
| | 4 | none | |
| group E | 1 | none | 0/4 |
| | 2 | none | |
| | 3 | none | |
| | 4 | none | |

*Pooled cervical ganglia cII, cIII and cIV

TABLE 4

Titre of latent challenge virus in the cervical ganglia after vaccination with inactivated WT HSV-1

| | Mouse no. | Virus titre in-cervical ganglia* ($\log_{10}$pfu WT) | reactivation frequency |
|---|---|---|---|
| group A | 1 | none | 3/4 |
| | 2 | 5.0 | |
| | 3 | 5.0 | |
| | 4 | 5.2 | |
| group B | 1 | 3.5 | 3/4 |
| | 2 | 4.0 | |
| | 3 | 5.5 | |
| | 4 | none | |
| group C | 1 | 3.6 | 2/4 |
| | 2 | 5.1 | |
| | 3 | none | |
| | 4 | none | |
| group D | 1 | none | 1/4 |
| | 2 | 4.8 | |
| | 3 | none | |
| | 4 | none | |
| group E | 1 | none | 0/4 |
| | 2 | none | |
| | 3 | none | |
| | 4 | none | |

*Pooled cervical ganglia cII, cIII and cIV
(p.f.u = plaque forming units; gH- is a virus with a defective gh gene).

These results show the titre of the challenge virus wt SC16 present in the ears and cervical ganglia during the acute phase of infection. Thus, a low titre indicates good effectiveness of the vaccination regimen with gH- virus whereas a higher titre, indicates poorer effectiveness. It is clear from the results that vaccination with live gH- HSV virus is very much more effective than an equivalent amount of inactivated WT virus. With the inactivated preparation, a dose of $5 \times 10^7$ pfu was required to prevent challenge virus replication in the ear, whereas with the live gH- virus, 100–1000 fold less virus was required. Live gH- virus vaccination with $5 \times 10^5$ pfu and over, was also able to block replication of the challenge virus in the cervical ganglia during the acute phase of infection, and furthermore showed a clear protective effect against the establishment of latent infection in the cervical ganglia.

HSV Lacking the gH Gene as a Vector for Immunisation Against a Foreign Antigen: Introduction of the gp120 Gene of SIVmac Strain 142 into the Genome of gH- HSV Virus Viruses with deletions in essential genes may, as described above, be used as safe vectors for the delivery of foreign antigens to the immune system, and the gH- HSV virus described above provides a suitable example of a such a vector. This virus could be used to express any desired foreign antigen, but a particularly attractive possibility would be the major antigenic proteins of the AIDS virus human immunodeficiency virus (HIV). Thus these sequences would be inserted into the gH- HSV genome in a way that would ensure their expression during infection of normal cells (i.e. non-complementing cells) by the recombinant virus. Infection of an individual with such a virus could lead to a latent infection which, from time to time upon reactivation, would lead to a burst of production of the foreign antigen, resulting in stimulation of the immune response to that protein.

Since studies to test this approach directly in humans are not feasible at present, as an initial stage, the approach may be tested in monkeys using the Simian AIDS virus $SIV_{mac}$ (Simian immunodeficiency virus isolated from macaques). A suitable SIV gene for this purpose is that encoding the gp120 protein, one of the major antigenic targets for this virus. This gene is therefore introduced into the gH- HSV genome, and the efficacy of this virus as a vaccine to protect monkeys against challenge with SIV assessed.

The SIV gp120 gene is first of all cloned next to the cytomegalovirus IE core promoter (Gompels and Minson, 1989, op. cit.), and subsequently a DNA cassette consisting of the gp120 gene and the upstream CMV promoter is cloned into plasmid pGH2 (FIG. 2). The resulting plasmid is then co-transfected into the gH+ complementing cell line along with DNA purified from the gH- HSV, and recombinant virus which has acquired the gp120 gene in place of the β-galactosidase gene present in the gH- HSV virus is isolated by screening for interruption of the β-galactosidase gene.

Figure 7:
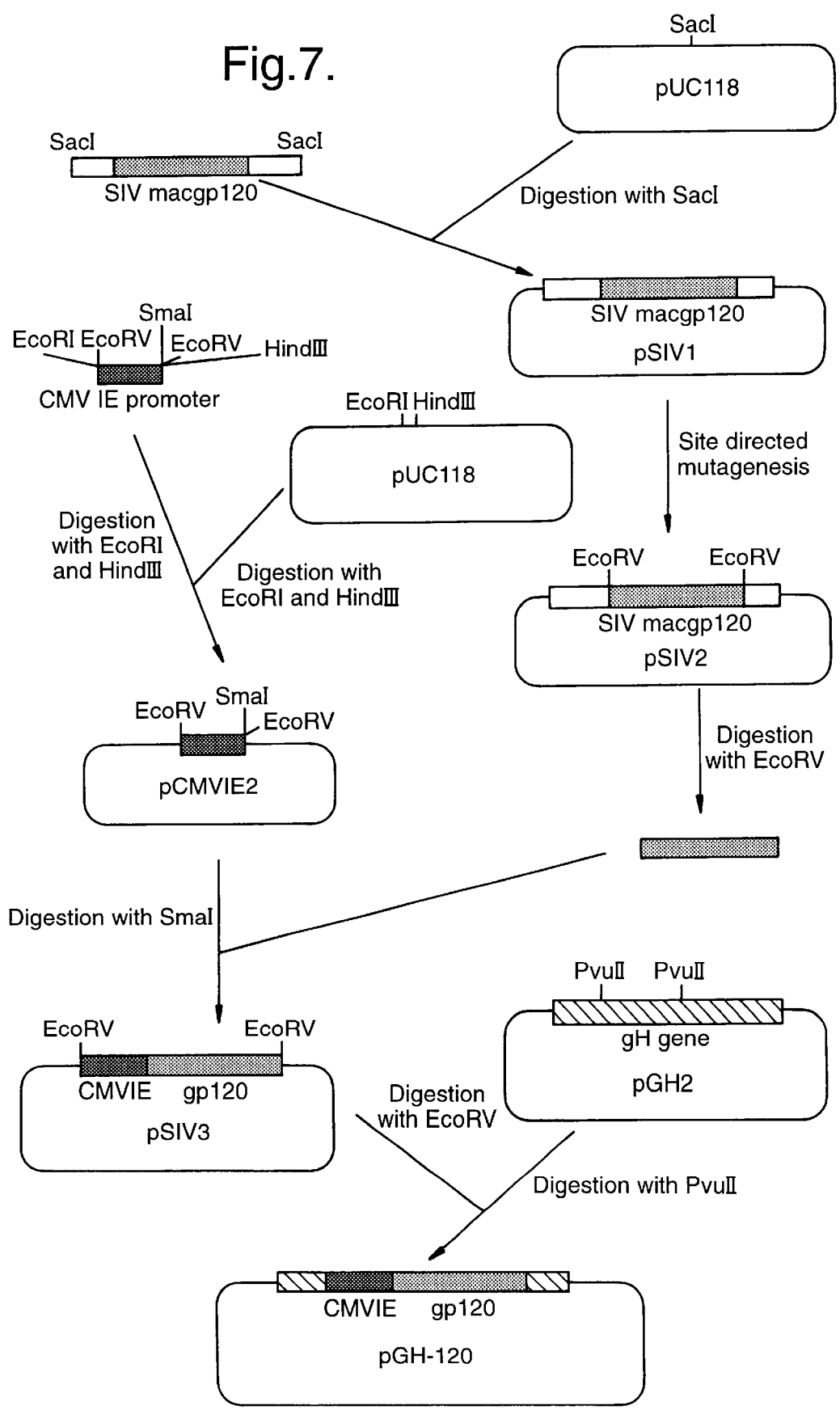
FIG. 7 illustrates the strategy for construction of plasmid pGH-120.

A. Construction of Plasmid for Recombination of the SIV gp120 Coding Sequence into the HSV Genome The overall scheme for this procedure is shown in FIG. 7. A SacI restriction enzyme fragment (corresponding to bases 5240–8721) is excised from a cloned DNA copy of the SIV genome (Chakrabarti et al., Nature 328, 543 (1987), and cloned into the SacI site of plasmid pUC118 (Viera and Messing, Methods in Enzymology, 153, 3, 1987) in order to generate plasmid pSIV1 which may be converted to single stranded DNA for manipulation by site directed mutagenesis. This DNA region, which includes the SIV env gene (lying between 6090–8298) is then altered by site directed mutagenesis (Brierley et al., Cell 57, 537, 1989) to introduce a restriction enzyme site for the enzyme EcoRV at positions 6053–6058 using the synthetic oligonucleotide (SEQ ID NO:6).

5'GAAGAAGGCTATAGCTAATACAT.

A second EcoRV site is then introduced at position 7671–7676 within the SIV env gene corresponding to the cleavage site between the gp120 and gp40 domains of the env gene sequence, using the synthetic oligonucleotide (SEQ ID NO:7).

5'CAAGAAATAAACTATAGGTCTTTGTGC to generate the plasmid pSIV2. A DNA fragment (1617 base pairs) corresponding to the gp120 portion of the SIV env gene is then prepared by digestion of SIV2 with EcoRV.

The core region of the CMV immediate early gene promoter is obtained from the plasmid pUG-H1 (Gompels and Minson, 1989, op cit.) by the PCR technique using the following two synthetic oligonucleotides (SEQ ID NO:8, SEQ ID NO:9).
upstream primer (SEQ ID NO:9)

5' ATC <u>GAATTC</u> <u>CTATAG</u> CCTGGCATTATGCCCAGTACATG
        EcoRI    EcoRV downstream primer 5'TCA<u>AAGCTT</u> <u>CTATAG</u> <u>CCCGGG</u>GAGCTCTGATTATATAGACCTCCC
       HindIII   EcoRV    SmaI The product of this reaction is then cleaved with the enzymes EcoRI and HindIII to generate a DNA fragment which is then cloned into EcoRI- and HindIII-digested plasmid pUC118 to generate the plasmid pCMVIE2 which has a unique SmaI site located just downstream of the CMV promoter sequence. The EcoRV fragment containing the $SIV_{mac}$ gp120 coding sequence prepared as described above, is then cloned into this SmaI site, and plasmid pSIV3, with the SIV coding region oriented correctly to allow expression of the coding sequence from the promoter, is then selected. This plasmid is then digested with EcoRV to yield a blunt-ended DNA fragment consisting of the SIV sequence together with the CMV promoter, which is then cloned into PvuII-digested pGH2 (FIG. 2) to produce pGH-120.

B. Construction of the SIV gp120 Carrying Recombinant gH− HSV

DNA is purified from the gH− HSV virus constructed as detailed in the previous section, and co-transfected into gH+ complementing cells along with purified pGH-120 DNA. Progeny virus isolated from this transection procedure is then plated on monolayers of the gH+ complementing cell line by standard plaque assay as before using an agar overlay in the presence of X-gal. The parental gH− virus carries a functional β-galactosidase gene, located within the residual gH coding sequences, and in the presence of X-gal, will form blue plaques. Recombinant viruses however, which have acquired the SIV gp120 coding sequence in place of the β-galactosidase gene, will produce white plaques. Virus is recovered from these white plaques by picking plugs of agar, and virus stocks prepared through growth of the virus in the gH+ complementing cell line. Virus DNA is prepared from these stocks, and checked for the presence of the correct DNA structure around the gH gene by Southern Blotting using appropriate probes derived from the SIV coding sequence. Finally stocks of the virus are prepared as before for vaccination studies in animals.

A vaccine comprising the attenuated virus can be prepared and used according to standard techniques known in the art. For example, the vaccine may also comprise one or more excipients and/or adjuvants. The effective dose of the attenuated virus to be provided by the vaccine may be determined according to techniques well known in the art.

What is claimed is:

1. A vaccine comprising a pharmaceutically acceptable excipient and an effective immunizing amount of a mutant herpesvirus, said mutant herpesvirus containing a genome in which a viral gene encoding a protein which is essential for the production of infectious virus has been deleted or inactivated, wherein said genome further includes a heterologous gene insert encoding an immunogenic protein, wherein said mutant virus is able to cause production of infectious new virus particles in a recombinant complementing host cell expressing a gene which complements said essential viral gene, but is unable to cause production of infectious new virus particles when said mutant virus infects a host cell other than said recombinant complementing host cell, for prophylactic or therapeutic use in generating an immune response in a subject infected therewith.

2. The vaccine of claim 1, wherein said heterologous gene insert encodes a protein from a pathogen.

3. The vaccine of claim 1, wherein said heterologous gene insert encodes a protein from SIV virus.

4. The vaccine of claim 1, wherein said essential gene encodes a protein involve in a post-replicative event.

5. The vaccine of claim 4, wherein said essential gene encodes a protein that is not required for virus assembly, but is necessary for the assembled virus to be able to infect new cells.

6. The vaccine of claim 1, which consists essentially of said pharmaceutically acceptable excipient and an effective immunizing amount of said mutant herpesvirus.

7. The vaccine of claim 1, wherein the mutant herpesvirus is capable of establishing a latent infection with periodic reactivation.

8. The vaccine of claim 1, wherein said essential gene which has been deleted or inactivated is a glycoprotein gene.

9. The vaccine of claim 1, wherein the herpesvirus is herpes simplex virus.

10. The vaccine of claim 9, wherein said herpesvirus is herpes simplex virus and the gene which has been deleted or inactivated is the gH gene.

11. The vaccine of claim 1, comprising a dose containing from about $5 \times 10^4$ pfu up to about $5 \times 10^7$ ptu of said mutant virus.

12. The vaccine of claim 11, comprising a dose containing from about $5 \times 10^4$ pfu up to about $5 \times 10^6$ pfu of said mutant virus.

13. The vaccine of claim 12, comprising a dose containing from about $5 \times 10^4$ pfu up to about $5 \times 10^5$ pfu of said mutant virus.

14. The vaccine of claim 1, wherein said mutant DNA virus is defective in more than one gene essential for production of infectious virus.

15. A method of manufacturing a vaccine according to claim 1, comprising the steps of:

a) growing a mutant herpesvirus in a recombinant complementing host cell, wherein said mutant herpesvirus contains a genome in which a viral gene encoding a protein which is essential for production of infectious virus has been deleted or inactivated, and said genome further includes a heterologous gene insert encoding an immunogenic protein, and said recombinant complementing host cell expresses a gene which complements said essential viral gene; and b) mixing the resulting virus in an effective immunizing amount with a pharmaceutically acceptable excipient.

16. The method of claim 15, wherein said heterologous gene insert encodes a protein from a pathogen.

17. The method of claim 15, wherein said heterologous gene insert encodes a protein from SIV virus.

18. The method of claim 15, wherein said essential protein is involved in a post-replicative event.

19. The method of claim 15, wherein said essential protein is not required for virus assembly, but is necessary for the assembled virus to be able to infect new cells.

20. The method of claim 15, wherein the mutant herpesvirus is capable of establishing a latent infection with periodic reactivation.

21. The method of claim 15, wherein said gene which has been deleted or inactivated is a glycoprotein gene.

22. The method of claim 15, 16, 17, 18, wherein the herpesvirus is herpes simplex virus.

23. The method of claim 21, wherein said herpesvirus is herpes simplex virus, and wherein the gene which has been deleted or inactivated is the gH gene.

24. The method of claim 23, comprising a dose containing from about $5 \times 10^4$ to about $5 \times 10^7$ pfu of said mutant virus.

25. The method of claim 23, comprising a dose containing from about $5 \times 10^4$ to about $5 \times 10^6$ pfu of said mutant virus.

26. The method of claim 23, comprising a dose containing from about $5 \times 10^4$ to about $5 \times 10^5$ pfu of said mutant virus.

27. The method of claim 23, wherein the mutant herpesvirus is defective in more than one gene essential for production of infectious virus.

28. A vaccine comprising a pharmaceutically acceptable excipient and an effective immunizing amount of an infectious virus, wherein the infectious virus in said vaccine consists essentially of a mutant herpesvirus containing a genome in which a viral gene encoding a protein which is essential for the production of infectious virus has been deleted or inactivated, wherein said genome further includes a heterologous gene insert encoding an immunogenic protein, wherein said mutant virus is able to cause production of infectious new virus particles in a recombinant complementing host cell expressing a gene which complements said essential viral gene, but is unable to cause production of infectious new virus particles when said mutant virus infects a host cell other than said recombinant complementing host cell, for prophylactic or therapeutic use in generating an immune response in a subject infected therewith.

29. A method comprising administering to a subject a vaccine comprising a pharmaceutically acceptable excipient and an effective immunizing amount of a mutant herpesvirus, said mutant herpesvirus containing a genome in which a viral gene encoding a protein which is essential for production of infectious virus has been deleted or inactivated, wherein said genome further includes a heterologous gene insert encoding an immunogenic protein, and wherein said mutant virus is able to cause production of infectious new virus particles in a recombinant complementing host cell expressing a gene which complements said essential viral gene, but is unable to cause production of infectious new virus particles when said mutant virus infects a host cell other than said recombinant complementing host cell, for prophylactic or therapeutic use in generating an immune response in a subject infected therewith.

30. The method of claim 29, wherein said heterologous gene insert, encodes a protein from a pathogen.

31. The method of claim 29, wherein said heterologous gene insert encodes a protein from SIV virus.

32. The method of claim 29, wherein said essential gene encodes a protein involved in a post-replicative event.

33. The method of claim 29, wherein said essential gene encodes a protein that is not required for virus assembly, but is necessary for the assembled virus to be able to infect new cells.

34. The method of claim 29, which said vaccine consists essentially of said pharmaceutically acceptable excipient and an effective immunizing amount of said mutant herpesvirus.

35. The method of claim 29, wherein the mutant herpesvirus is capable of establishing a latent infection with periodic reactivation.

36. The method of claim 29, wherein said essential gene which has been deleted or inactivated is a glycoprotein gene.

37. The method of claim 29, 30, 31, 32, 34, 36, wherein the herpesvirus is herpes simplex virus.

38. The method of claim 37, wherein said herpesvirus is herpes simplex virus and wherein the gene which has been deleted or inactivated is the gH gene.

39. The method of claim 29, wherein said vaccine comprises a dose containing from about $5\times10^4$ to about $5\times10^7$ pfu of said mutant virus.

40. The method of claim 39, wherein said vaccine comprises a dose containing from about $5\times10^4$ to about $5\times10^6$ pfu of said mutant virus.

41. The method of claim 39, wherein said vaccine comprises a dose containing from about $5\times10^4$ to about $5\times10^5$ pfu of said mutant virus.

42. The method of claim 29, wherein the mutant herpesvirus is defective in more than one gene essential for production of infectious virus.

43. A method comprising administering to a subject a vaccine comprising a pharmaceutically acceptable excipient and an effective immunizing amount of an infectious virus, wherein the infectious virus in said vaccine consists essentially of a mutant herpesvirus containing a genome in which a viral gene encoding a protein which is essential for production of infectious virus has been deleted or inactivated, where said genome further includes a heterologous gene insert encoding an immunogenic protein, and wherein said mutant virus is able to cause production of infectious new virus particles in a recombinant complementing host cell expressing a gene which complements said essential viral gene, but is unable to cause production of infectious new virus particles when said mutant virus infects a host cell other than said recombinant complementing host cell, for prophylactic or therapeutic use in generating an immune response in a subject infected therewith.

* * * * *

UNITED STATES PATENT AND TRADEMARK OFFICE
CERTIFICATE OF CORRECTION

PATENT NO. : 6,541,009 B1
DATED : April 1, 2003
INVENTOR(S) : Inglis et al.

It is certified that error appears in the above-identified patent and that said Letters Patent is hereby corrected as shown below:

Column 7,
Lines 63-64, "(SEQ ID NO:1, SEQ ID NO:2)" should read
-- (SEQ ID NO:4, SEQ ID NO:5) --.

Column 13,
Line 5, "upstream primer (SEQ ID NO:9)" should read
-- upstream primer (SEQ ID NO:8) --.
Line 10, "downstream primer" should read
-- downstream primer (SEQ ID NO:9) --.

Signed and Sealed this

Eleventh Day of May, 2004

JON W. DUDAS
*Acting Director of the United States Patent and Trademark Office*